(12) United States Patent
Fan et al.

(10) Patent No.: US 12,235,271 B2
(45) Date of Patent: Feb. 25, 2025

(54) MOLECULAR TYPING OF MULTIPLE MYELOMA AND APPLICATION

(71) Applicant: BEIJING NORMAL UNIVERSITY, Beijing (CN)

(72) Inventors: Xiaolong Fan, Beijing (CN); Ayaz Ali Samo, Beijing (CN); Jiuyi Li, Beijing (CN); Xuzhang Lu, Beijing (CN)

( * ) Notice: Subject to any disclaimer, the term of this patent is extended or adjusted under 35 U.S.C. 154(b) by 1105 days.

(21) Appl. No.: 17/049,667

(22) PCT Filed: Apr. 25, 2019

(86) PCT No.: PCT/CN2019/084241
§ 371 (c)(1),
(2) Date: Oct. 22, 2020

(87) PCT Pub. No.: WO2019/206217
PCT Pub. Date: Oct. 31, 2019

(65) Prior Publication Data
US 2021/0055301 A1  Feb. 25, 2021

(30) Foreign Application Priority Data

Apr. 28, 2018 (CN) .......................... 201810399756.6
Apr. 28, 2018 (CN) .......................... 201810401708.6

(51) Int. Cl.
| | | |
|---|---|---|
| *G01N 33/574* | (2006.01) | |
| *G01N 33/50* | (2006.01) | |
| *G16B 25/00* | (2019.01) | |
| *G16B 40/00* | (2019.01) | |
| *G16H 50/30* | (2018.01) | |

(52) U.S. Cl.
CPC ... *G01N 33/57484* (2013.01); *G01N 33/5011* (2013.01); *G16B 25/00* (2019.02); *G16B 40/00* (2019.02); *G16H 50/30* (2018.01)

(58) Field of Classification Search
None
See application file for complete search history.

(56) References Cited

U.S. PATENT DOCUMENTS

2017/0159130 A1    6/2017   Mitra et al.

FOREIGN PATENT DOCUMENTS

| WO | 2010/078531 A2 | 7/2010 |
| WO | 2013/007795 A1 | 1/2013 |

OTHER PUBLICATIONS

Roepman et al An Immune Response Enriched 72-Gene Prognostic Profile for Early-Stage Non Small-Cell Lung Cancer Clin Cancer Res 2009;15(1) Jan. 1, 2009 doi:10.1158/1078-0432.CCR-08-1258.*
Van Laar et al. Translating a gene expression signature for multiple myeloma prognosis into a robust high-throughput assay for clinical use BMC Medical Genomics 2014, 7:25 http://www.biomedcentral.com/1755-8794/7/25.*
Kuiper, R., et al., "A gene expression signature for high-risk multiple myeloma" Leukemia (2012) 26:2406-2413.
Samo, A.A., et al., "MCL1 gene co-expression module stratifies multiple myeloma and predicts response to proteasome inhibitor-based therapy" Genes Chromosomes Cancer (2018) 57:420-429.
Vangsted, et al., "Drug response prediction in high-risk multiple myeloma" Gene (2018) 644:80-86.
Decaux, et al., "Bortezomib Inhibits mTOR Pathway in Multiple Myeloma Cell Lines Via Induced Expression of REDD1" Blood (2007) 110 (11):242.

* cited by examiner

*Primary Examiner* — Joseph Woitach
(74) *Attorney, Agent, or Firm* — Robert C. Netter, Jr.; Dann, Dorfman, Herrell & Skillman (57) ABSTRACT

Disclosed are molecular typing of multiple myeloma and application thereof. Specifically, disclosed is a product comprising a substance for obtaining or detecting 97 gene expressions in multiple myeloma patients to be detected and an apparatus for operating a multiple myeloma Bayesian classifier. By using the product, the present invention identifies a gene module co-expressed with the MCL1 gene, thereby distinguishing molecular subtypes of multiple myeloma having different prognoses and bortezomib sensitivities.

6 Claims, 6 Drawing Sheets

MOLECULAR TYPING OF MULTIPLE MYELOMA AND APPLICATION

This application is a § 371 application of PCT/CN2019/084241, filed Apr. 25, 2019, which in turn claims priority to CN application No. 201810401708.6, filed Apr. 28, 2018, and CN application No. 201810399756.6, filed Apr. 28, 2018. The entire disclosure of each of the foregoing applications is incorporated by reference herein.

TECHNICAL FIELD

The invention belongs to the field of biotechnology, and in particular relates to a molecular classification and application of multiple myeloma.

BACKGROUND ART

Multiple myeloma (MM) is the second most common haematological malignancy caused by abnormal proliferation of plasma cells. The incidence of MM is estimated to be 1-2 cases/100,000 people in China. The majority of MMs occur in elderly population of over 60 years of age. Within an aging population in China, MM incidence increases over time, and becomes a severe health risk to the elderly populations. MMs are typically manifested by excessive proliferation of abnormal plasma cells, and the secretion of abnormal immunoglobulin protein or fragments of immunoglobulin protein, which is referred to as M protein. M protein concentration is an important diagnostic indicator of MM.

The development of proteasome inhibitor bortezomib and immunomodulatory agents, such as lenadomine and thalidomide, has significantly improved the survival of patients with MM. However, MMs are yet incurable. MMs exhibit extensive heterogeneities in their biological and clinical features. Consequently, the response and survival improvement of the combined treatment of multiple drugs vary substantially among patients with MM. Their underlying mechanisms have not been understood, which hinders the development of individualised treatment. To improve understanding of MM biology, and to facilitate treatment decision, it is important to develop a simple and reliable molecular classification method for MM. Several molecular classification schemes have been proposed. For example, Bergsagel et al. have proposed a classification scheme with 8 MM subtypes on the basis of different cyclin D expression and chromosomal translocations. Based on unbiased transcriptome analysis, Zhan et al. and Broyl et al. have proposed 7 to 10 molecular subtypes for MMs. Based on the length of the patient survival; these subtypes were further simplified as high-risk group and low-risk group. In addition, prognosis-related gene expression profiles, e.g.: UAMS-70, UAMS-17, UAMS-80, IFM-15, Millennium-100, EMC-92, gene amplification index GPI-5, MRC-IX-6, and centrosome amplification index have also been proposed.

However, the above-mentioned molecular classification schemes and gene expression profiles did not predict treatment response, and failed to correlate molecular classification with plasma cell development. Furthermore, no attempt was made to correlate the classify genes with MM pathogenesis.

SUMMARY OF THE INVENTION

In order to better reveal the cytological origin of multiple myeloma and provide targeted treatment for multiple myeloma, the present invention provides the following technical solutions:

An object of the present invention is to provide the use of obtaining or detecting the expression of 97 genes in patients with multiple myeloma to be tested.

The present invention provides an application of a substance for obtaining or detecting the expression of 97 genes in a patient with multiple myeloma to be tested in preparing products for predicting the prognosis of the patients with multiple myeloma to be tested.

The survival outcomes include survival rate, survival length and extent of survival risk.

The survival rate includes the overall survival rate and progression free survival rate.

The present invention further provides an application of a substance for obtaining or detecting the expression of 97 genes in patients with multiple myeloma to be tested in preparing a product with at least one of the following a-c functions:

a) detecting the effect of bortezomib or bortezomib-containing treatment in patients with MM;
  b) detecting the sensitivity of bortezomib or bortezomib-containing treatment in patients with MM;
  c) directing bortezomib or bortezomib-containing treatment for patients with MM.

Another object of the present invention is to provide the use of a substance for obtaining or detecting the expression of 97 genes in patients with multiple myeloma (MM) to be tested or an apparatus for running a Bayesian classifier of multiple myeloma.

The present invention provides an application of a substance for obtaining or detecting the expression of 97 genes in patients with multiple myeloma (MM) to be tested or an apparatus for running a Bayesian classifier of multiple myeloma in the preparation of a product for predicting the prognosis of patients with multiple myeloma to be tested.

The prognosis is reflected in a prognostic survival rate, a length of survival or a degree of survival risk.

The present invention further provides an application of a substance for obtaining or detecting the expression of 97 genes in patients with multiple myeloma (MM) to be tested or an apparatus for running a Bayesian classifier of multiple myeloma in preparing products in the preparation of products with at least one of the following a-c functions:

a. detection of an efficacy of bortezomib or bortezomib-containing treatment in patients with MM;
  b. detection of a sensitivity of bortezomib or bortezomib-containing treatment in patients with MM;
  c. direction for administration of bortezomib or bortezomib-containing treatment in patients with MM;

the 97 genes comprising: ACBD3, ADAR, ADSS, ALDH2, ANP32E, ANXA2, ATF3, ATP8B2, CACYBP, CAPN2, CCND1, CCT3, CDC42SE1, CERS2, CHSY3, CLIC1, CLMN, COPA, CSNK1G3, DAP3, DENND1B, ENSA, EPRS, EPSTI1, EVL, FAM13A, FAM49A, FLAD1, FRZB, GLRX2, HAX1, HDGF, HLA-A, HLA-B, HLA-C, HLA-F, HLA-G, IL6R, ISG20L2, JTB, KLF2, LAMTOR2, LDHA, MCL1, MOXD1, MRPL24, MRPL9, MVP, MYL6, NDUFS2, NOP58, NOTCH2NL, NTAN1, PAK1, PI4KB, PIEZO1, PIK3AP1, PIM2, PIP5K1B, PMVK, POGZ, PPIA, PRCC, PRKCA, PRRC2C, PSMB4, PSMD4, RAB29, RCBTB2, SCAMP3, SCAPER, SDHC, SEL1L3, SELPLG, SHC1, SIDT1, SSR2, STAP1, TAP1, TIMM17A, TLR10, TMCO1, TOR1AIP2, TOR3A, TP53INP1, TPM3, TRANK1, TROVE2, UAP1, UBE2Q1, UBQLN4, UHMK1, VPS45, YY1AP1, ZC3H11A, ZFP36, and ZNF593; and the Bayesian classifier of multiple myeloma is obtained by a method comprising the following steps:
1) obtaining the expression data of the 97 classifier genes in n MM samples;
the 97 gene expression data of MM samples are derived from existing databases or the 97 gene expression data of multiple myeloma samples constructed with more than 100 samples;
n is greater than or equal to 100;
the expression levels of 97 genes are the expression levels of 97 genes in multiple myeloma cells;
2) assigning the MM samples into an MCL1-M high subtype or an MCL1-M low subtype by consensus clustering;
3) employing a naïve Bayes method to construct the Bayesian classifier on the basis of the two subtypes of step 2), the 97 gene expression data of n multiple myeloma samples in step 1), and prognostic survival data of the n multiple myeloma samples, an naïve Bayesian method is used to construct the Bayesian classifier.

In step 3) above, first the n multiple myeloma samples is divide randomly into a training set and a validation set according to the ratio of the number of samples greater than 1:1; and then the expression data of the 97 genes are used in the training, the MCL1-M-High and MCL1-M-Low subtype tag of each sample are obtained with the Consensus Clustering algorithm, next, the naïve Bayes algorithm in the R language machine learning package klaR is used to build a Bayesian classifier for multiple myeloma that predicts the MCL1-M-High and MCL1-M-Low subtypes of a single patient.

The above-mentioned method of obtaining the expression data of the 97 genes of each multiple myeloma sample is to detect the expression of 97 genes of the multiple myeloma sample or obtain the expression of the 97 genes of the multiple myeloma sample from a database.

A third object of the present invention is to provide a product.

The products provided by the present invention include an apparatus for obtaining or detecting the expression of 97 genes in multiple myeloma patients and running multiple myeloma Bayesian classifiers (the apparatus can be a CD or a computer, etc.).

As for the above products, the product has at least one of the following functions:
The product has at least one of the following 1) to 4) functions:
1) predicting the prognosis of patients with multiple myeloma to be tested;
2) detecting the sensitivity of patients with multiple myeloma to bortezomib or a drug containing bortezomib;
3) detecting an efficacy of bortezomib or a drug containing bortezomib in the patients with multiple myeloma to be tested;
4) instructing the patients with multiple myeloma to be tested for administration of bortezomib or medications containing bortezomib.

The product further comprises a carrier for recording a detection method.

The detection method comprises the following steps: obtaining or detecting the expression of 97 genes in the multiple myeloma patient to be tested to obtain the expression data of the 97 genes in the multiple myeloma patient to be tested; and then classifying the expression data of 97 genes in the multiple myeloma patient to be tested with a Bayes classifier of multiple myeloma, wherein the predicted prognosis of patients with multiple myeloma belonging to an MCL1-M-High subtype is significantly poorer than that of patients with multiple myeloma belonging to an MCL1-M-Low subtype;

or, the detection method comprises the following steps: obtaining or detecting the expression of 97 genes in the multiple myeloma patient to be tested to obtain the expression data of the 97 genes in the multiple myeloma patient to be tested; and then classifying the expression data of 97 genes in the multiple myeloma patient to be tested with a Bayes classifier of multiple myeloma, wherein the predicted prognosis of patients with multiple myeloma belonging to an MCL1-M-High subtype is better than that of patients with multiple myeloma belonging to an MCL1-M-Low subtype;

or, the detection method comprises the following steps: obtaining or detecting the expression of 97 genes in the multiple myeloma patient to be tested to obtain the expression data of the 97 genes in the multiple myeloma patient to be tested; and then classifying the expression data of 97 genes in the multiple myeloma patient to be tested with a Bayes classifier of multiple myeloma, wherein if the patient with multiple myeloma to be tested belongs to an MCL1-M-High subtype, bortezomib or drugs containing bortezomib are used for treatment; if the patient with multiple myeloma to be tested belongs to an MCL1-M-Low subtype, bortezomib or bortezomib-containing drugs are not used for treatment.

In the product mentioned above, the multiple myeloma patients to be tested is a single patient or a plurality of patients.

In the above product, the n multiple myeloma samples are 551 samples;
or the ratio greater than 1:1 mentioned above is to randomly divide the training set and the verification set according to a ratio of 2:1.

A fourth object of the present invention is to provide a method for constructing a model for classifying multiple myeloma patients.

The method provided by the present invention includes the following steps:
1) obtaining the expression data of the 97 classifier genes in n MM samples;
the 97 gene expression data of MM samples are derived from existing databases or the 97 gene expression data of multiple myeloma samples constructed with more than 100 samples;
n is greater than or equal to 100;
the expression levels of 97 genes are the expression levels of 97 genes in multiple myeloma cells;
2) assigning the MM samples into an MCL1-M high subtype or an MCL1-M low subtype by consensus clustering;
3) employing a naïve Bayes method to construct the Bayesian classifier on the basis of the two subtypes of step 2), the 97 gene expression data of n multiple myeloma samples in step 1), and prognostic survival data of the n multiple myeloma samples, an naïve Bayesian method is used to construct the Bayesian classifier, so as to obtain a target model.

The 97 gene expressions in multiple myeloma patients were derived from the 97 gene expression in tumour cells of the multiple myeloma patients.

The foregoing method for obtaining or detecting the expression of 97 genes in a patient with multiple myeloma to be tested and/or the device for running the multiple myeloma Bayesian classifier or the model obtained by the foregoing method is used to predict the multiple bone marrow to be tested The application of the prognostic survival rate of multiple myeloma patients is also the protection scope of the present invention.

The 97 gene expressions in multiple myeloma patients were derived from the 97 gene expression in tumour cells of multiple myeloma patients.

The foregoing apparatus for obtaining or detecting the substance expressed by 97 genes in a patient with multiple myeloma to be tested and/or for operating the Bayesian classifier of multiple myeloma, or the application of the model obtained by the above method in the preparation of products for predicting the prognostic survival rate of patients with multiple myeloma to be tested are all within the scope of protection of the present invention.

The foregoing apparatus for obtaining or detecting the substance expressed by 97 genes in a patient with multiple myeloma to be tested and/or for operating the Bayesian classifier of multiple myeloma, or the application of the model obtained by the above method in the preparation of products for predicting the prognostic survival of patients with multiple myeloma to be tested are all within the scope of protection of the present invention.

The foregoing apparatus for obtaining or detecting the substance expressed by 97 genes in a patient with multiple myeloma to be tested and/or for operating the Bayesian classifier of multiple myeloma, or the application of the model obtained by the above method in the preparation of products for predicting the degree of survival risk of patients with multiple myeloma to be tested are all within the scope of protection of the present invention.

The present invention also provides a method for classifying multiple myeloma patients, which includes the following steps:
  obtaining or detecting the expression of 97 genes in the multiple myeloma patient to be tested to obtain the expression data of the 97 genes in the multiple myeloma patient to be tested; and then classifying the expression data of 97 genes in the multiple myeloma patient to be tested with a Bayes classifier of multiple myeloma, so as to determine whether the patient with multiple myeloma to be tested belongs to the MCL1-M-High subtype or the MCL1-M-Low subtype.

The present invention further provides a method for predicting the prognosis of patients with multiple myeloma to be tested, comprising the following steps: obtaining or detecting the expression of 97 genes in the multiple myeloma patient to be tested to obtain the expression data of the 97 genes in the multiple myeloma patient to be tested; and then classifying the expression data of 97 genes in the multiple myeloma patient to be tested with a Bayes classifier of multiple myeloma; the predicted prognosis of patients with multiple myeloma belonging to an MCL1-M-High subtype is significantly poor than or poor than that of patients with multiple myeloma belonging to an MCL1-M-Low subtype.

The prognosis is reflected in a prognostic survival rate, a length of survival or a degree of survival risk.

The predicted prognosis of patients with multiple myeloma belonging to the MCL1-M-High subtype is significantly poor than that of patients with multiple myeloma belonging to the MCL1-M-Low subtype, which is re-elected as at least one of the following 1) to 3):
  1) the predicted prognostic survival rate of patients with multiple myeloma to be tested belonging to the MCL1-M-High subtype is significantly lower than that of patients with multiple myeloma to be tested belonging to the MCL1-M-Low subtype;
  2) the predicted prognostic survival of patients with multiple myeloma to be tested belonging to the MCL1-M-High subtype is significantly lower than that of patients with multiple myeloma to be tested belonging to the MCL1-M-Low subtype;
  3) the predicted degree of survival risk of patients with multiple myeloma to be tested belonging to the MCL1-M-High subtype is significantly lower than that of patients with multiple myeloma to be tested belonging to the MCL1-M-Low subtype.

The present invention provides the detection of an efficacy of bortezomib or a drug containing bortezomib for a patient with multiple myeloma to be tested, comprising the following steps: obtaining or detecting the expression of 97 genes in the multiple myeloma patient to be tested to obtain the expression data of the 97 genes in the multiple myeloma patient to be tested; and then classifying the expression data of 97 genes in the multiple myeloma patient to be tested with a Bayes classifier of multiple myeloma, wherein the predicted prognosis of patients with multiple myeloma belonging to an MCL1-M-High subtype is better than that of patients with multiple myeloma belonging to an MCL1-M-Low subtype.

The present invention provides the direction for administration of bortezomib or a drug containing bortezomib for a patient with multiple myeloma to be tested, comprising the following steps: obtaining or detecting the expression of 97 genes in the multiple myeloma patient to be tested to obtain the expression data of the 97 genes in the multiple myeloma patient to be tested; and then classifying the expression data of 97 genes in the multiple myeloma patient to be tested with a Bayes classifier of multiple myeloma, wherein if the patient with multiple myeloma to be tested belongs to an MCL1-M-High subtype, bortezomib or drugs containing bortezomib are used for treatment; if the patient with multiple myeloma to be tested belongs to an MCL1-M-Low subtype, bortezomib or bortezomib-containing drugs are not used for treatment.

The expression of the 97 classifier genes can be obtained from MM databases, or directly detected from MM samples.

The expression levels of the above-mentioned genes are the gene expression levels in multiple myeloma tumour cells.

DETAILED DESCRIPTION OF PREFERRED EMBODIMENTS

All of the experimental methods used in the following Examples are conventional methods unless otherwise indicated.

All of the materials, reagents, etc. used in the following Examples are commercially available unless otherwise indicated.

Example 1. Screening of Molecular Diagnostic Markers for Multiple Myeloma and Implementation of Molecular Typing From the MM gene expression dataset GSE2658 published by NCBI, a gene module co-expressed with MCL1 (MCL1-M), containing 87 genes, was identified using Pearson correlation coefficient analysis. Based on the foregoing, 46 genes upregulated in MM samples with low expression of MCL1-M were also identified. For stable classification outcomes, 36 genes among the above-mentioned 133 genes with low classification capacity were excluded, 97 genes with robust differential expression with relatively high level of expression were selected.

These 97 genes are as follows: ACBD3, ADAR, ADSS, ALDH2, ANP32E, ANXA2, ATF3, ATP8B2, CACYBP, CAPN2, CCND1, CCT3, CDC42SE1, CERS2, CHSY3, CLIC1, CLMN, COPA, CSNK1G3, DAP3, DENND1B, ENSA, EPRS, EPSTI1, EVL, FAM13A, FAM49A, FLAD1, FRZB, GLRX2, HAX1, HDGF, HLA-A, HLA-B, HLA-C, HLA-F, HLA-G, IL6R, ISG20L2, JTB, KLF2, LAMTOR2, LDHA, MCL1, MOXD1, MRPL24, MRPL9, MVP, MYL6, NDUFS2, NOP58, NOTCH2NL, NTAN1, PAK1, PI4KB, PIEZO1, PIK3AP1, PIM2, PIP5K1B, PMVK, POGZ, PPIA, PRCC, PRKCA, PRRC2C, PSMB4, PSMD4, RAB29, RCBTB2, SCAMP3, SCAPER, SDHC, SEL1L3, SELPLG, SHC1, SIDT1, SSR2, STAP1, TAP1, TIMM17A, TLR10, TMCO1, TOR1AIP2, TOR3A, TP53INP1, TPM3, TRANK1, TROVE2, UAP1, UBE2Q1, UBQLN4, UHMK1, VPS45, YY1AP1, ZC3H11A, ZFP36, and ZNF593.

These 97 genes were selected as classifier genes for classification. Based on the expression data of these 97 genes, the 551 MM samples in GSE2658 were clustered into MCL1-M high and MCL1-M low subtype using consensus clustering. However, clustering-based method does not enable classification of individual samples. To enable classification of individual MM samples, the 551 samples were randomly split into a training set (369 samples) and a validation set (182 samples) at a ratio of 2:1. The stratified sampling process was guided by the results of consensus clustering, to ensure the proportion of MCL1-M high and MCL1-M samples in the training and validation sets remains the same as in the original dataset.

Based on the expression data of these 97 classifier genes in the 369 samples from the training set, and the subtyping results of MCL1-M high or MCL1-M low to these samples in consensus clustering, Bayes classification for assigning individual MM samples into the MCL1-M high or MCL1-M low subtype was trained using naïve Bayes classification algorithm with the klaR package of R.

The codes of MM Bayes classifier are as follows:

```
options(warn=-1)
# install machine learning package klaR
install.packages("klaR")
# load expression data of 97 classifier genes in GSE2658 from file and pre-processing
library(klaR)
i=0
while(TRUE){
  GSE2658.data<-read.delim("gse2658.batch_removed.txt", row.names=1,stringsAsFactors = T)
  GSE2658<-apply(GSE2658.data[,-1], 1,scale)
  GSE2658<-t(GSE2658)
  GSE2658<-data.frame(GSE2658.data[,1],GSE2658)
  colnames(GSE2658)[1]<-'subtype'
  colnames(GSE2658)<-colnames(GSE2658.data)
  rownames(GSE2658)<-rownames(GSE2658.data)
# split samples into training set and validation set at a ratio of 2:1
  while (TRUE){
    split_train_test<-function(data,ratio){
      train_indices<-sample(length(data[,1]),as.integer(length(data[,1])*ratio))
      return(train_indices)
    }
    train_sets<-GSE2658[split_train_test(GSE2658,0.67),]
test_sets<-GSE2658[-split_train_test(GSE2658,0.67),
# Construction of naïve Bayes classification model using the training set
    GSE2658.NB<-NaiveBayes(subtype ~.,data=train_sets,fL=1)
    if(as.vector(GSE2658.NB$apriori)[1]<0.453&as.vector(GSE2658.NB$apriori[1])>0.451){
      break
    }
  }
# Verification of the power of naïve Bayes classification model in the validation set
  results<-predict(GSE2658.NB,test_sets[,-1],threshold = 0.1,type='raw')
  predicted_class<-as.data.frame(results)
  predicted_class[,2:3]<-apply(predicted_class[,2:3],2,round,3)
# Identification of naïve Bayes classification model with an accuracy rate > 97% using cross labelling process
  compare_table<-data.frame(predicted_class$class,test_sets$subtype)
  colnames(compare_table)<-c("predicted_class","original_class")
  table<-prop.table(table(compare_table),2)
  accuracy=c(table[1,1],table[2,2])
  if(accuracy[1]>0.95&accuracy[2]>0.95){
    break
  }
```

-continued

```
  else)
  i=i+1
  }
}
print(paste('Both sensitivity and Specifity gets greater than 0.97 at the', i,'th','trial',sep=' '))
# Bayes classification-based subtype Prediction in MMRF data set
mmrf.data<-read.delim("mmrf.batch_removed.txt", row.names=1,stringsAsFactors = T)
mmrf<-apply(mmrf.data[,-1], 1,scale)
mmrf<-t(mmrf)
rownames(mmrf)<-rownames(mmrf.data)
colnames(mmrf)<-colnames(mmrf.data)[-1]
mmrf<-data.frame(mmrf.data$subtype,mmrf)
colnames(mmrf)[1]<-'subtype'
results.mmrf<-predict(GSE2658.NB,mmrf[,-1],threshold = 0.01,type='raw')
predicted_class.mmrf<-as.data.frame(results.mmrf)
predicted_class.mmrf[,2:3]<-apply(predicted_class.mmrf[,2:3],2,round,3)
compare_table.mmrf<-data.frame(predicted_class.mmrf$class,mmrf.data$subtype)
colnames(compare_table.mmrf)<-c("predicted_class","original_class")
prop.table(table(compare_table.mmrf),2)
# Bayes classification-based subtype Prediction in GSE19784 data set
gse19784.data<-read.delim("gse19784.batch_removed.txt", row.names=1,stringsAsFactors = T)
gse19784<-apply(gse19784.data[,-1], 1,scale)
gse19784<-t(gse19784)
colnames(gse19784)<-colnames(gse19784.data)[-1]
gse19784<-data.frame(gse19784.data$subtype,gse19784)
colnames(gse19784)[1]<-'subtype'
results_19784<-predict(GSE2658.NB,gse19784[,-1],threshold = 0.01,type='raw')
predicted_class_19784<-as.data.frame(results_19784)
predicted_class_19784[,2:3]<-apply(predicted_class_19784[,2:3],2,round,3)
compare_table_19784<-data.frame(predicted_class_19784$class,gse19784$subtype)
colnames(compare_table_19784)<-c("predicted_class","original_class")
prop.table(table(compare_table_19784),2)
```

Moreover, 182 samples in the validation set were used to evaluate the accuracy of the classification.

Figure 1:
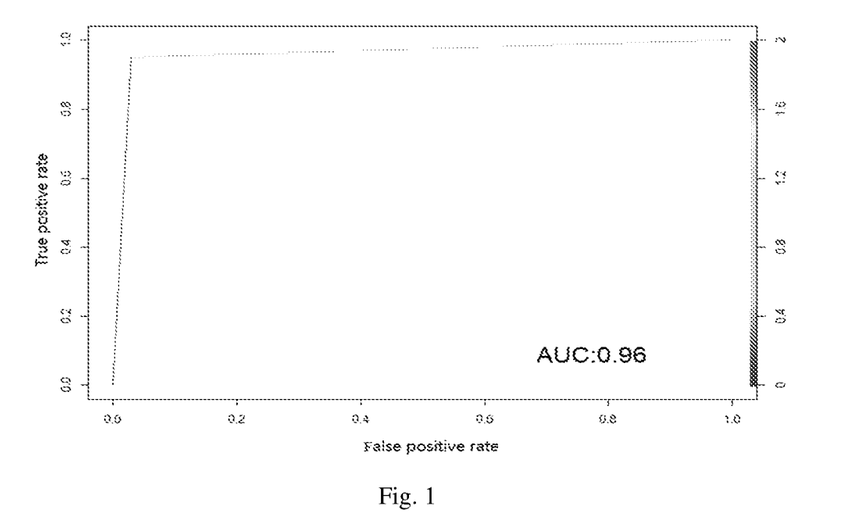
FIG. 1 is a plot of ROC curve for the Bayes classification in GSE2658 data set.

Bayes classification model was optimised using the accuracy results of each run, until the accuracy was greater than 95%. The accuracy results for Bayes classification in GSE2658 is presented in Table 1, and the ROC curve data in FIG. 1.

TABLE 1

Accuracy of Naïve Bayes prediction model in GSE2658

| | | Molecular subtyping based on unsupervised Consensus Clustering | |
|---|---|---|---|
| | Subtype | MCL1-M-High | MCL1-M-Low |
| Molecular subtyping predicted by naïve Bayes model | MCL1-M-High | 77 | 3 |
| | MCL1-M-Low | 4 | 98 |
| | Accuracy | 95.1% | 97.0% |

For testing whether naïve Bayes model developed using data from GSE2658 could be generally used, the applicant used naïve Bayes model in MM data set MMRF published by NCI and the GEO MM data set GSE19784.

Figure 2:
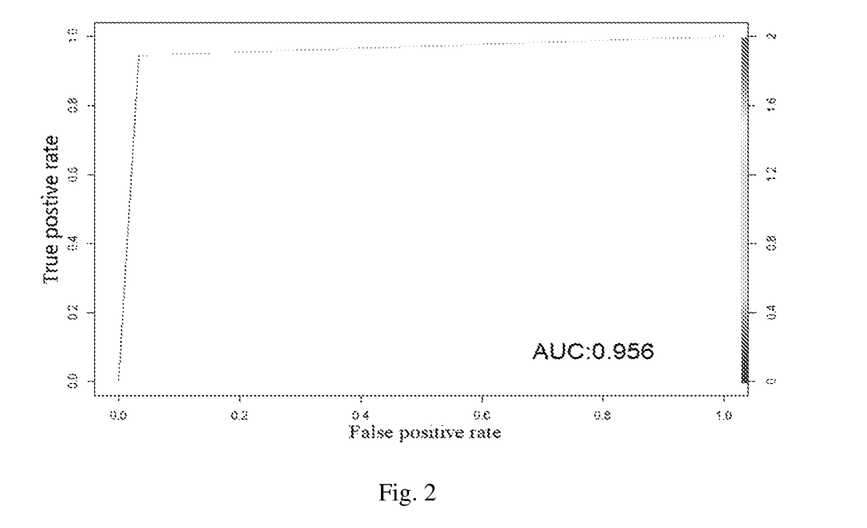
FIG. 2 is a plot of ROC curve for the Bayes classification in MMRF data set.

The MMRF data set was different from GSE2658, as the expression data were obtained from mRNA-seq. Bayes classification model for MMRF data set is presented in Table 2, and the ROC curve plot in FIG. 2.

TABLE 2

Accuracy of naïve Bayes prediction model established with GSE2658 data set in MMRF data set

| | | Molecular subtyping based on unsupervised consensus clustering | |
|---|---|---|---|
| | Subtype | MCL1-M-High | MCL1-M-Low |
| Molecular subtyping predicted by naïve Bayes model | MCL1-M-High | 240 | 11 |
| | MCL1-M-Low | 4 | 323 |
| | accuracy | 94.5% | 96.7% |

The results show that even for cross-platform, the classifier can maintain high accuracy, which shows that it has a high value for promotion and application.

Figure 3:
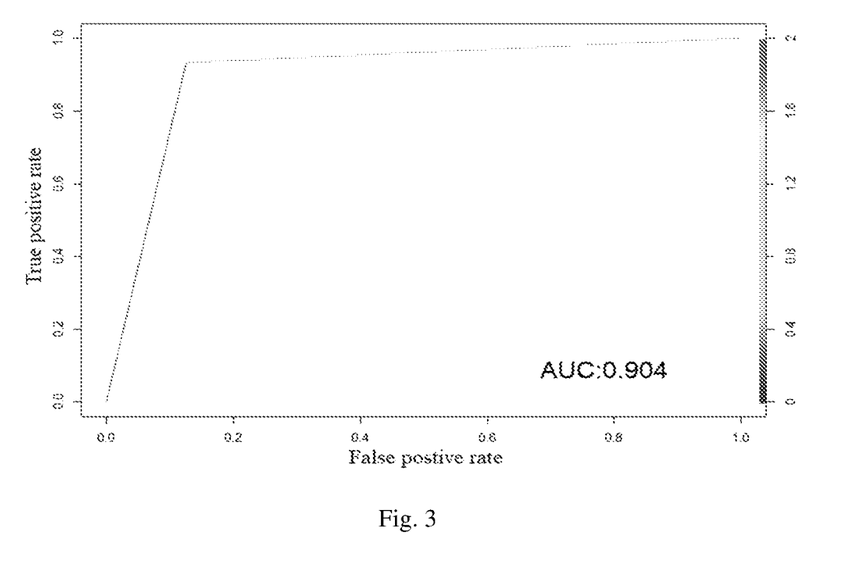
FIG. 3 is a plot of ROC curve for the Bayes classification in GSE19784 data set.

Similar to GSE2658, expression data in data set GSE19784 were also generated using Affymetrix U133 2.0 plus 2.0 platform. GSE19784 was generated by different laboratories and at different time period, the experimental conditions are unlikely the same as for GSE2658, the two data sets may thereby have different dynamics and noise in gene expression profile. The results of naïve Bayes prediction in GSE19784 is shown in Table 3 and the ROC curve plot in FIG. 3. Accurate classification results were also generated in data set GSE19784.

TABLE 3

The accuracy of the classifier built using the GSE2658
data set in the GSE19784 data set

| | Subtype | Molecular subtyping based on unsupervised consensus clustering | |
|---|---|---|---|
| | | MCL1-M-High | MCL1-M-Low |
| Molecular subtyping predicted by naïve Bayes model | MCL1-M-High | 98 | 25 |
| | MCL1-M-Low | 7 | 174 |
| | accuracy | 93.3% | 87.4% |

The results show that the classifier can better overcome the above-mentioned problems and still maintain high accuracy.

Example 2. Application of Naïve Bayes Prediction Model in the Prediction of Survival of Patients with MM I. Data Set GSE2658

Based on the expression data of the 97 classifier genes in 551 pre-treated MM samples in GSE2658 database, the 551 samples were classified using the Naïve Bayes prediction model developed in Example 1, resulting in 249 MCL1-M high MMs and 302 MCL1-M low MMs.

Figure 4:
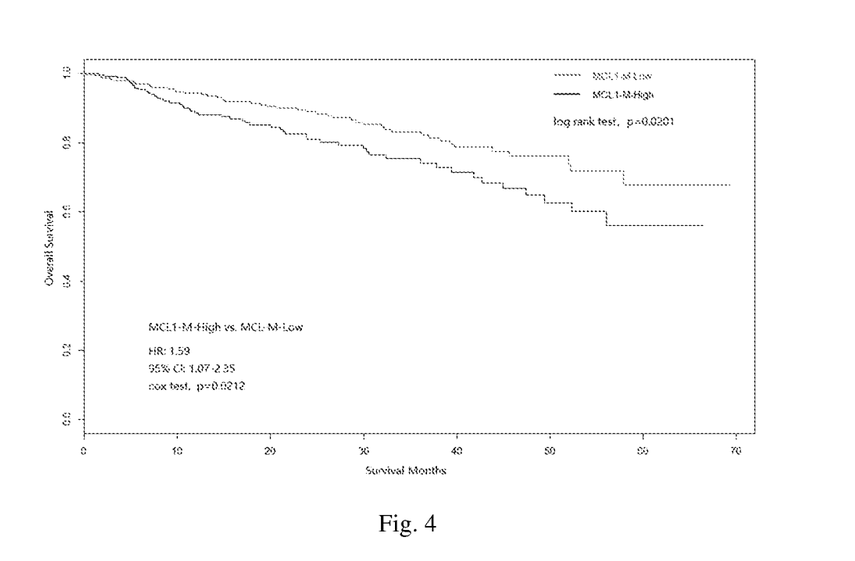
FIG. 4 is an overall survival of patients with MCL1-M high MM or MCL1-M low MM in GSE2658.

The follow-up time for 551 patients of MMs was 72 months. The results of survival analysis (Kaplan-Meier analysis and Cox regression analysis) are shown in FIG. 4. Distinct survival was observed between MCL1-M high and MCL1-M low subtypes, the overall survival in patients with MCL1-M high MM was significantly lower compared with the overall survival in patients with MCL1-M low MM (log-rank test, p=0.0201; hazard ratio 1.588, p=0.0212).

Thus, based on the expression of the 97 classifier genes in MCL1 gene group, the naïve Bayes prediction model enabled the prediction of prognosis of patients with MM.

II. Database MMFR

Based on the expression data of the 97 classifier genes in 534 pre-treated MM samples (pre-treatment testing), molecular classification was performed using the naïve Bayes prediction model developed in Example 1, resulting in 231 MCL1-M high MMs and 303 MCL1-M low MMs in the classification of the 534 samples.

Figure 5:
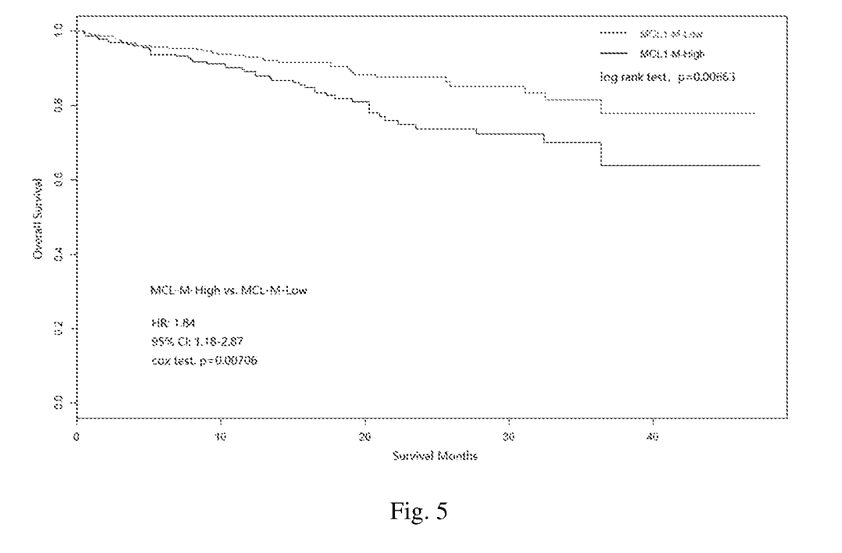
FIG. 5 is an overall survival of patients with MCL1-M high MM or MCL1-M low MM in in GSE2658.

The follow-up time for 534 patients of MMs was 48 months. The results of survival analysis (Kaplan-Meier analysis and Cox regression analysis) are shown in FIG. 5. Distinct survival was observed between MCL1-M high and MCL1-M low subtypes, the overall survival in patients with MCL1-M high MM was significantly lower compared with the overall survival in patients with MCL1-M low MM (log-rank test, p=0.006663; hazard ratio 1.838, p=0.00706).

Thus, irrespective of the technical platform for the detection of expression data, the expression of the 97 classifier genes and the naïve Bayes prediction model enabled the prediction of prognosis of patients with MM.

III. Database GSE19784

Based on the expression data of the 97 classifier genes in 304 pre-treated MM samples in the database GSE19784, molecular classification was performed using the naïve Bayes prediction model developed in Example 1, resulting in 107 MCL1-M high MMs and 196 MCL1-M low MMs.

Figure 6A:
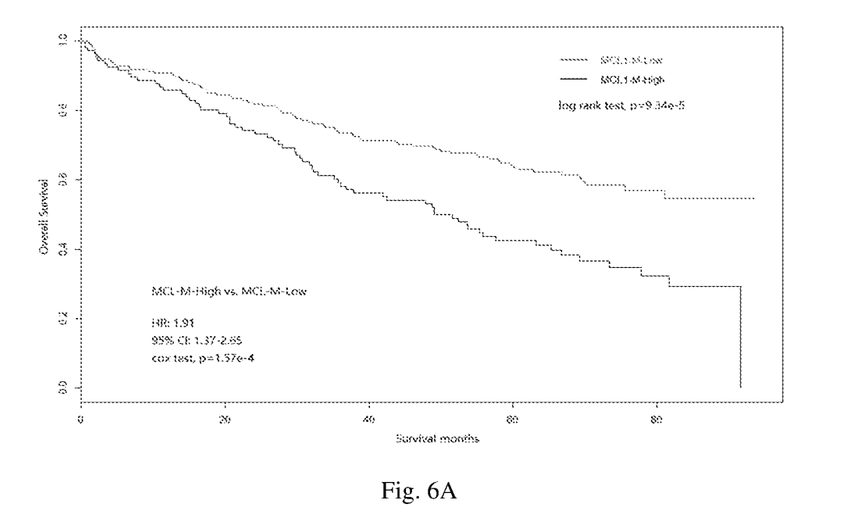
FIGS. 6A and 6B show the overall survival (FIG. 6A) and progression-free survival (FIG. 6B) of patients with MCL1-M high MM or MCL1-M low MM in GSE19784.
Figure 6B:
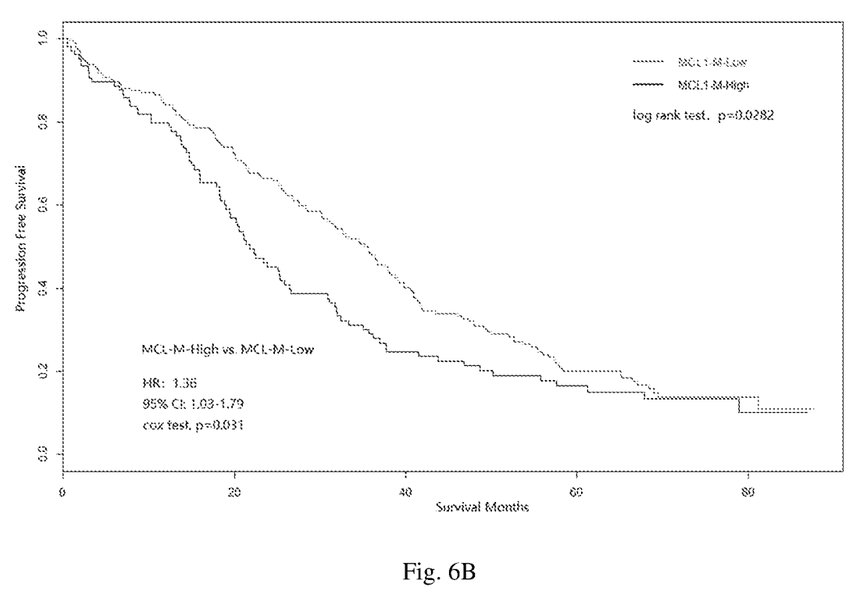
Figure 7A:
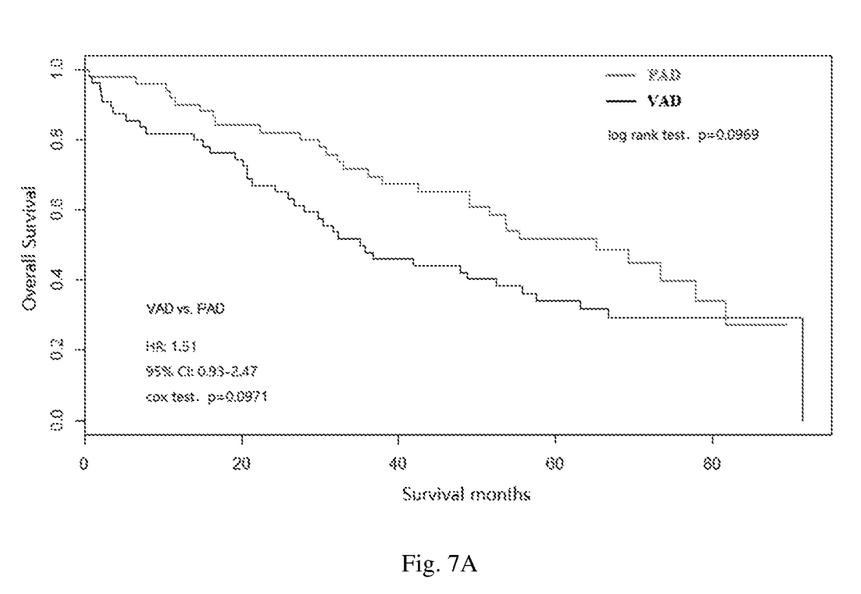
FIGS. 7A to 7D show distinct responses of patients with MCL1-M high MM or MCL1-M low MM to bortezomib-containing treatment in GSE19784.
Figure 7B:
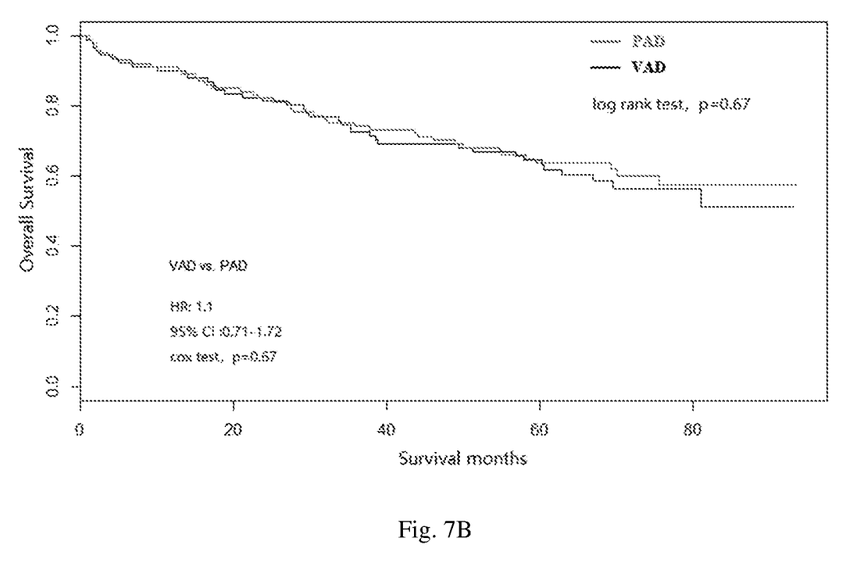
Figure 7C:
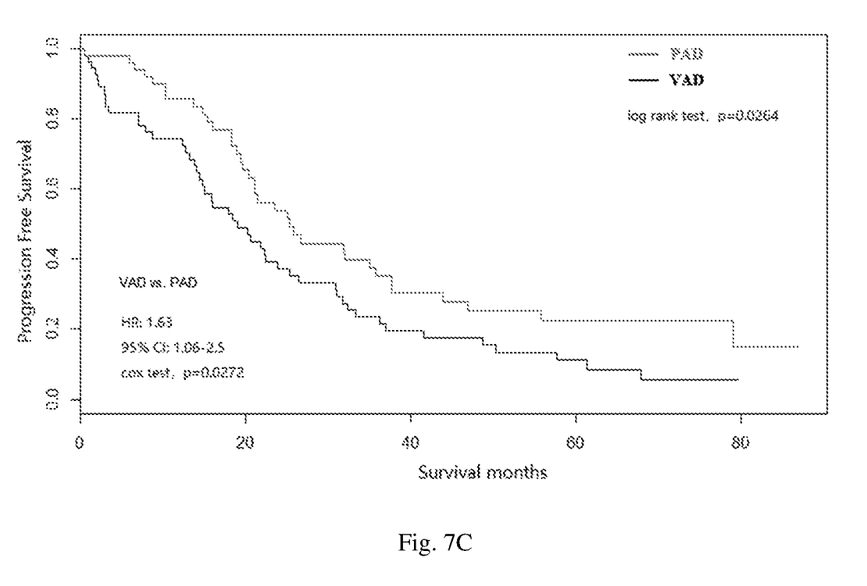
Figure 7D:
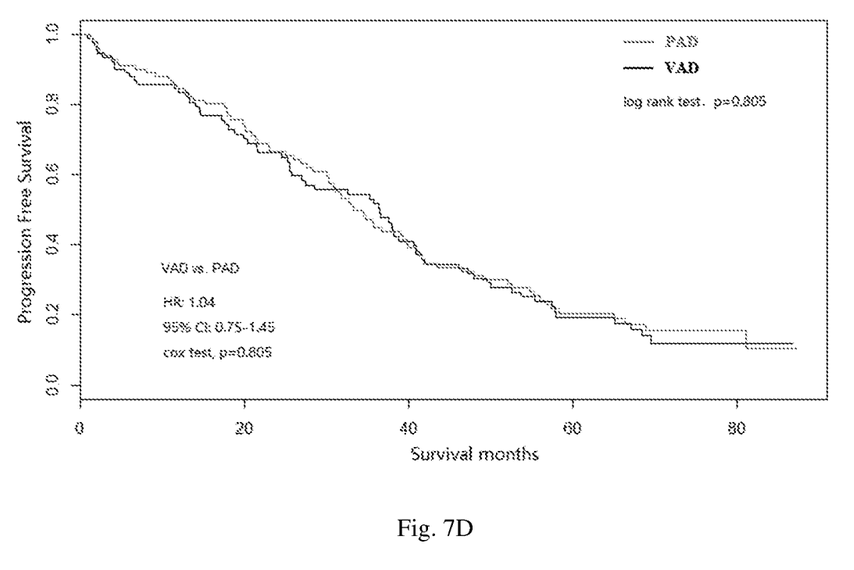

The follow-up time for 304 patients of MMs was 96 months. The results of survival analysis (Kaplan-Meier analysis and Cox regression analysis) are shown in FIG. 6 (panel A for overall survival; panel B for progression free survival). Distinct survival was observed between MCL1-M high and MCL1-M low subtypes, the overall survival in patients with MCL1-M high MM was significantly lower compared with the overall survival in patients with MCL1-M low MM (log-rank test, p<0.0001; hazard ratio 1.91, p=0.0002). GSE19784 also contains progression-free survival data. Similarly, progression-free survival in patients with MCL1-M high MM was significantly lower compared with progression-free survival in patients with MCL1-M low MM (log-rank test, p=0.0282; Likelihood ratio test, hazard ratio 1.36, p=0.031). These results confirm that the expression of the 97 classifier genes and the naïve Bayes prediction model enabled the prediction of prognosis of patients with MM.

Example 3. The Molecular Diagnostic Markers and Classification of Multiple Myeloma are Predicting Whether the Test Patient can be Treated with Bortezomib The gene expression data in GSE19784 were generated from MM patients enrolled in a randomised phase III clinical trial (the HOVON-65/GMMG-HD4 trial), the treatment details for all patients were documented. The patients were randomly assigned into the two groups receiving either a drug combination of VAD (vincristine, doxorubicin, and dexamethasone; 155 patients) or PAD (bortezomib, doxorubicin, and dexamethasone; 148 patients). The difference therebetween is that the PAD combination contains bortezomib. All the expression data were derived from samples before treatment.

Using naïve Bayes prediction model, the MM samples were classified as the MCL1-M high and MCL1-M low subtype (as described in Example 1). The survival analysis (Kaplan-Meier analysis and Cox regression analysis) were separately analysed in MCL1-M high samples (51 with PAD treatment; 56 with VAD treatment); or MCL1-M low samples (104 MMs with PAD treatment; 92 MMs with VAD treatment) according to the treatment options.

The results are shown in FIG. 7, panel A for overall survival in MCL1-M high subtype, panel B for overall survival in MCL1-M low subtype, panel C for progression-free survival in MCL1-M high subtype, panel D for progression-free survival in MCL1-M low subtype. Bortezomib-based PAD treatment only prolonged the survival of patients with MCL1-M high MM, particularly the progression-free survival (FIG. 7, left panel, MCL-M high subtype, right panel, MCL-M low subtype; Upper: overall survival curve, Lower: progression-free survival curve). This shows bortezomib-based PAD treatment can postpone the progression of MCL1-M high MM, but for patient with MCL-M low MM, bortezomib-based PAD treatment does not show any effect. In summary, this invention enables the stratification of patients with MM for treatment decisions, which can avoid the treatment of MCL1-M low MM with bortezomib. This reduces treatment-related economic burden and prevents treatment-induced side effects.

Example 4. Application of Naïve Bayes Prediction Model in Stratifying Patients with MM into Different Risk Groups Bone marrow samples of 30 newly diagnosed MMs were collected at Beijing Chaoyang hospital. CD138+ cells were purified using anti-CD138 antibody-coated beads and used to generate total RNA. The RNA preparations were hybridised with Affymetrix Prime View array for detection of the expression of the 97 classifier genes.

Consensus clustering was performed to identify the MCL1-M high or MCL-M low samples in group; naïve Bayes prediction model developed in Example 1 was performed to identify the MCL1-M high or MCL1-M low samples individually.

As shown in Table 4, the classifying results of consensus clustering and naïve Bayes prediction model were highly concordant. Only 1 MCL1-M high MM was predicted as MCL-M low MM, suggesting that naïve Bayes prediction model can be utilised for prediction of MM subtypes in individual samples.

Because of the limitations in the size of data set and the short follow-up period, survival analysis was not performed. However, based on the traditional risk parameters (existing medical certification index), the 19 MCL1-M high MMs contained 14 high risk MMs defined by the traditional risk parameters, and the 11 MCL1-M low MMs contained only 3 high risk MMs defined by the traditional risk parameters. This shows that in this example, the established classification can still predict the patient's prognosis.

TABLE 4

Accuracy of the classifier built using the GSE2658 data set in the collected samples

|  |  | Molecular subtyping based on unsupervised Consensus Clustering | |
| --- | --- | --- | --- |
|  | Subtype | MCL1-M-High | MCL1-M-Low |
| Molecular subtyping predicted by naïve Bayes model | MCL1-M-High | 18 | 0 |
|  | MCL1-M-Low | 1 | 11 |
|  | accuracy | 94.7% | 100% |

INDUSTRIAL APPLICABILITY

Current molecular classification schemes do not correlate to the cellular origin of MM, also fail to predict treatment effect. The present invention has explored gene co-expression networks around key signalling pathways of germinal centre development for understanding MM etiology and molecular classification of MM. The applicant has screened for dys-regulated gene networks involved in the development from B cells to plasma cells, because these networks potentially play important roles in MM pathogenesis. Following a series of analyses, the applicant identified gene co-expression module around MCL1 (MCL1-M), developed a classification scheme to assign MMs into the MCL-M high or MCL-M low subtype. These two subtypes are distinct in their prognosis and patterns of genomic alterations. More importantly, this classification scheme predicts response to bortezomib treatment, and correlates to plasma cell development. The current invention constitutes a new platform for the development of individualised precision therapy against MM, also improves the understanding of MM pathogenesis.

The invention claimed is:

1. A method for predicting the prognosis of patients with multiple myeloma (MM), wherein the method comprises:
    obtaining a Bayesian classifier of MM by a method comprising the following steps:
    1) obtaining the expression data of 97 classifier genes in n MM samples, wherein the 97 classifier genes comprise: ACBD3, ADAR, ADSS, ALDH2, ANP32E, ANXA2, ATF3, ATP8B2, CACYBP, CAPN2, CCND1, CCT3, CDC42SE1, CERS2, CHSY3, CLIC1, CLMN, COPA, CSNK1G3, DAP3, DENND1B, ENSA, EPRS, EPSTI1, EVL, FAM13A, FAM49A, FLAD1, FRZB, GLRX2, HAX1, HDGF, HLA-A, HLA-B, HLA-C, HLA-F, HLA-G, IL6R, ISG20L2, JTB, KLF2, LAMTOR2, LDHA, MCL1, MOXD1, MRPL24, MRPL9, MVP, MYL6, NDUFS2, NOP58, NOTCH2NL, NTAN1, PAK1, PI4 KB, PIEZO1, PIK3AP1, PIM2, PIP5K1B, PMVK, POGZ, PPIA, PRCC, PRKCA, PRRC2C, PSMB4, PSMD4, RAB29, RCBTB2, SCAMP3, SCAPER, SDHC, SEL1L3, SELPLG, SHC1, SIDT1, SSR2, STAP1, TAP1, TIMM17A, TLR10, TMCO1, TOR1AIP2, TOR3A, TP53INP1, TPM3, TRANK1, TROVE2, UAP1, UBE2Q1, UBQLN4, UHMK1, VPS45, YY1AP1, ZC3H11A, ZFP36, and ZNF593;
    2) Assigning the MM samples into an MCL1-M high subtype or an MCL1-M low subtype by consensus clustering; and
    3) employing a naïve Bayes method to construct the Bayesian classifier on the basis of the two subtypes of step 2), the 97 classifier gene expression data of n MM samples in step 1), and prognostic survival data of the n MM samples;
    obtaining or detecting the expression of 97 classifier genes in the patients with MM;
    predicting, using the constructed Bayesian classifier, the prognosis of the patients with MM and the treatment effect of using bortezomib or bortezomib-containing drug combinations, wherein the constructed Bayesian classifier determines whether the patient with MM belongs to the MCL1-M high subtype or the MCL1-M low subtype, and wherein the predicted prognosis of the patient with MM belonging to the MCL1-M high subtype is significantly poorer than that of the patient with MM belonging to the MCL1-M low subtype; and
    treating the patient with MM determined to belong to the MCL1-M high subtype by the constructed Bayesian classifier with bortezomib or a bortezomib-containing drug combination.

2. The method according to claim 1, wherein the prognosis is reflected in a prognostic survival rate or a length of survival.

3. An apparatus for running a Bayesian classifier of multiple myeloma (MM) to predict the prognosis of patients with MM,
    wherein the apparatus comprises a carrier for recording a detection method, wherein the detection method comprises the following steps:
    obtaining or detecting the expression of 97 classifier genes in a MM patient to be tested to obtain the expression data of the 97 classifier genes in the MM patient to be tested, wherein the 97 classifier genes comprise: ACBD3, ADAR, ADSS, ALDH2, ANP32E, ANXA2, ATF3, ATP8B2, CACYBP, CAPN2, CCND1, CCT3, CDC42SE1, CERS2, CHSY3, CLIC1, CLMN, COPA, CSNK1G3, DAP3, DENND1B, ENSA, EPRS, EPSTI1, EVL, FAM13A, FAM49A, FLAD1, FRZB, GLRX2, HAX1, HDGF, HLA-A, HLA-B, HLA-C, HLA-F, HLA-G, IL6R, ISG20L2, JTB, KLF2, LAMTOR2, LDHA, MCL1, MOXD1, MRPL24, MRPL9, MVP, MYL6, NDUFS2, NOP58, NOTCH2NL, NTAN1, PAK1, PI4 KB, PIEZO1, PIK3AP1, PIM2, PIP5K1B, PMVK, POGZ, PPIA, PRCC, PRKCA, PRRC2C, PSMB4, PSMD4, RAB29, RCBTB2, SCAMP3, SCAPER, SDHC, SEL1L3, SELPLG, SHC1, SIDT1, SSR2, STAP1, TAP1, TIMM17A, TLR10, TMCO1, TOR1AIP2, TOR3A, TP53INP1, TPM3, TRANK1, TROVE2, UAP1, UBE2Q1, UBQLN4, UHMK1, VPS45, YY1AP1, ZC3H11A, ZFP36, and ZNF593; and classifying the expression data of 97 classifier genes in the MM patient to be tested with a Bayes classifier of MM; wherein the predicted prognosis of patients with MM belonging to an MCL1-M-High subtype is significantly poorer than that of patients with MM belonging to an MCL1-M-Low subtype;

wherein if the patient with MM to be tested belongs to an MCL1-M-High subtype, bortezomib or drug combinations containing bortezomib are used for treatment; if the patient with MM to be tested belongs to an MCL1-M-Low subtype, bortezomib or bortezomib-containing drug combinations are not used for treatment;

wherein a prediction of an efficacy of bortezomib or bortezomib-containing drug combinations of patients with MM belonging to the MCL1-M high subtype is better than that of patients with MM belonging to the MCL1-M low subtype based on a prognostic survival rate or a length of survival; and wherein the Bayes classifier is obtained by a method comprising the following steps:

1) obtaining the expression data of the 97 classifier genes in n MM samples,
2) Assigning MM samples into an MCL1-M high subtype or an MCL1-M low subtype by consensus clustering, and
3) employing a naïve Bayes method to construct the Bayesian classifier on the basis of the two subtypes of step 2), the 97 classifier gene expression data of n MM samples in step 1), and prognostic survival data of the MM samples.

4. The apparatus according to claim 3, wherein the MM patients to be tested is a single patient or a plurality of patients.

5. A method of constructing a model for classifying multiple myeloma (MM) patients, comprising the following steps:

1) Obtaining the expression data of 97 classifier genes in n MM samples, wherein the 97 genes comprise: ACBD3, ADAR, ADSS, ALDH2, ANP32E, ANXA2, ATF3, ATP8B2, CACYBP, CAPN2, CCND1, CCT3, CDC42SE1, CERS2, CHSY3, CLIC1, CLMN, COPA, CSNK1G3, DAP3, DENND1B, ENSA, EPRS, EPSTI1, EVL, FAM13A, FAM49A, FLAD1, FRZB, GLRX2, HAX1, HDGF, HLA-A, HLA-B, HLA-C, HLA-F, HLA-G, IL6R, ISG20L2, JTB, KLF2, LAMTOR2, LDHA, MCL1, MOXD1, MRPL24, MRPL9, MVP, MYL6, NDUFS2, NOP58, NOTCH2NL, NTAN1, PAK1, PI4 KB, PIEZO1, PIK3AP1, PIM2, PIP5K1B, PMVK, POGZ, PPIA, PRCC, PRKCA, PRRC2C, PSMB4, PSMD4, RAB29, RCBTB2, SCAMP3, SCAPER, SDHC, SEL1L3, SELPLG, SHC1, SIDT1, SSR2, STAP1, TAP1, TIMM17A, TLR10, TMCO1, TOR1AIP2, TOR3A, TP53INP1, TPM3, TRANK1, TROVE2, UAP1, UBE2Q1, UBQLN4, UHMK1, VPS45, YY1AP1, ZC3H11A, ZFP36, and ZNF593;

2) Assigning the MM samples into an MCL1-M high subtype or an MCL1-M low subtype by consensus clustering; and
3) employing a naïve Bayes method to construct the Bayesian classifier on the basis of the two subtypes of step 2), the 97 classifier gene expression data of n MM samples in step 1), and prognostic survival data of the n MM samples, wherein the constructed naïve Bayesian prediction model determines whether the patient with MM belongs to the MCL1-M high subtype or the MCL1-M low subtype, wherein the predicted prognosis of the patient with MM belonging to the MCL1-M high subtype is significantly poorer than that of the patient with MM belonging to the MCL1-M low subtype;

wherein if the patient with MM belongs to the MCL1-M high subtype, bortezomib or bortezomib-containing drug combinations are used for treatment, and if the patient with MM belongs to the MCL1-M low subtype, bortezomib or bortezomib-containing drug combinations are not used for treatment; and wherein the treatment effect of using bortezomib or bortezomib-containing drug combinations prolongs the survival rate or a length of survival for the patient with MM belonging to the MCL1-M high subtype.

6. A naïve Bayes classifier prepared by the method according to claim 5.

* * * * *